United States Patent
Wright

(10) Patent No.: US 6,668,621 B1
(45) Date of Patent: Dec. 30, 2003

(54) VISCOSITY MEASUREMENT BY MEANS OF DAMPED RESONANT VIBRATION NORMAL TO AN APPROXIMATE RIGID PLATE

(76) Inventor: Hubert Arthur Wright, 10 Girard Rd., Winchester, MA (US) 01890

( * ) Notice: Subject to any disclaimer, the term of this patent is extended or adjusted under 35 U.S.C. 154(b) by 6 days.

(21) Appl. No.: 10/170,071

(22) Filed: Jun. 13, 2002

(51) Int. Cl.$^7$ .............................................. G01N 11/10
(52) U.S. Cl. .................... 73/54.25; 73/54.41; 73/54.26; 73/54.23
(58) Field of Search ............................ 73/54.23, 54.24, 73/54.25, 54.26, 54.27, 54.38, 54.41

(56) References Cited

U.S. PATENT DOCUMENTS

| | | | |
|---|---|---|---|
| 2,865,197 A | * 12/1958 | Penther et al. ............. | 73/54.22 |
| 3,062,040 A | * 11/1962 | McKennell et al. ........ | 73/54.24 |
| 3,194,064 A | * 7/1965 | Miles ......................... | 73/54.39 |
| 3,349,604 A | 10/1967 | Banks | |
| 3,603,137 A | 9/1971 | Banks | |
| 4,026,671 A | 5/1977 | Simons et al. | |
| 4,166,381 A | * 9/1979 | Woo ........................... | 73/54.25 |
| 4,524,610 A | 6/1985 | Fitzgerald et al. | |
| 4,552,012 A | 11/1985 | Bohlin | |
| 4,558,588 A | 12/1985 | Beaudoin et al. | |
| 4,695,956 A | 9/1987 | LeVeen et al. | |
| 4,926,682 A | * 5/1990 | Holm-Kennedy et al. . | 73/54.01 |
| 5,157,962 A | 10/1992 | Fitzgerald et al. | |
| 5,228,331 A | 7/1993 | Odagiri et al. | |
| 5,253,513 A | 10/1993 | Van Arsdale et al. | |
| 5,455,475 A | 10/1995 | Josse et al. | |
| 5,509,298 A | * 4/1996 | Cheema ...................... | 73/54.41 |
| 5,710,374 A | 1/1998 | Ross et al. | |
| 5,723,771 A | 3/1998 | Miura et al. | |
| 5,750,884 A | 5/1998 | Field | |
| 5,892,143 A | * 4/1999 | Namerikawa et al. ..... | 73/54.24 |
| 5,955,659 A | * 9/1999 | Gupta et al. ............... | 73/54.01 |
| 6,023,961 A | 2/2000 | Discenzo et al. | |
| 6,044,694 A | 4/2000 | Anderson et al. | |
| 6,112,581 A | 9/2000 | Scheider et al. | |
| 6,250,136 B1 | 6/2001 | Igreja | |
| 6,269,686 B1 | * 8/2001 | Hahn et al. ................ | 73/54.24 |
| 6,311,549 B1 | 11/2001 | Thundat et al. | |

FOREIGN PATENT DOCUMENTS

JP 04357439 A * 12/1992 ................ 73/54.41

* cited by examiner

Primary Examiner—Edward Lefkowitz
Assistant Examiner—Michael Cygan

(57) ABSTRACT

A brief but intense magnetic impulse generated by a coil 42 is used to excite resonant bending mode vibration in a magnetically permeable cantilevered beam 2 immersed in a fluid 22. A permanent magnet 36 and a magnetically permeable circuit 44, 38, 40, 56, 32, 6, and 2 enhance the magnetic coupling between the flexible beam 2 and the coil 42. A rigid post 6, positioned close to the beam and normal to the plane of oscillation is used to substantially increase the shearing induced in the fluid and thereby the rate of viscous attenuation of the vibrating beam. Oscillation of the vibrating beam 2 is detected by the same coil 42 that initiated the vibrations. The rate of decay of the vibrations is related to absolute viscosity.

14 Claims, 6 Drawing Sheets

VISCOSITY MEASUREMENT BY MEANS OF DAMPED RESONANT VIBRATION NORMAL TO AN APPROXIMATE RIGID PLATE

BACKGROUND OF THE INVENTION

1. Field of the Invention

The invention is concerned with techniques for vibratory measurement of the viscosity of fluids, particularly techniques which are capable of measurement of low viscosity fluids using devices suitable for continuous measurement in a flowing stream, commonly referred to as a process viscometer.

2. Background Information

Knowledge of the viscosity of a fluid is of great practical interest in many technical areas, including the measurement and control of printing inks, fuels, lubricants, paints, and coatings. In many cases, such as fuel, lubricant and ink measurement, there is a need for continuous measurement of low viscosity fluid (perhaps 5 to 20 centipoise), while operating in a demanding, high noise environment.

There have been developed many commercial, scientific, and laboratory techniques for viscosity measurement. In all cases, it is necessary to induce a shearing motion in the fluid, since viscosity is a measure of the resistance of a fluid to shear. In some devices that shearing motion is induced by vibration.

One vibratory technique is to twist or flex a tube, or bar, or probe immersed in or containing the fluid under test. For example, U.S. Pat. No. 4,525,610 describes a tube which contains the fluid which is twisted and flexed. U.S. Pat. Nos. 5,228,331, 5,723,771, 6,112,581 and 6,250,136 describe a tube or shaft with a paddle which is twisted in torsion. U.S. Pat. Nos. 4,026,671 and 5,710,374 describe the use of a rod which is vibrated axially while immersed in a fluid. In each case creation and measurement of torsional force and motion is relatively complicated and the systems are generally not sufficiently accurate at low viscosities.

In U.S. Pat. Nos. 6,269,686 B1 and 6,311,549 B1 there are described micro-machined devices in which a small cantilevered element is vibrated.

U.S. Pat. Nos. 5,253,513 and 5,750,884 describe laboratory devices in which the fluid is contained between two plates. A broadband, quasi-random force is imposed on one plate, normal to the face of the plate. Instruments are then used to measure the force, measure the resulting displacement, then to analyze the two waveforms in the frequency domain to determine viscosity. These laboratory devices are complex and not well suited to continuous process measurement.

SUMMARY OF THE INVENTION

I have developed a simple two wire viscometer with good sensitivity to even low viscosity fluids using vibrational techniques. I excite flexural motion of a cantilever beam using a brief impulsive electromagnetic force generated by a coil in magnetic proximity to the beam. A magnet is mounted on the beam which couples into the coil to increase the magnetic coupling to the coil and to create electromotive force in the coil as the beam vibrates. A magnetic circuit is also used to improve the coupling. In order to increase the viscous damping effects of the fluid to enable accurate measurement of low viscosities, the flexible beam is positioned close to a rigid post. The fluid in the gap between the beam and the post is sheared as a result of beam vibration normal to the post. The shearing motion of the fluid results in viscous retardation of the flexible beam and attenuation of the vibration. Detection circuitry measures the rate of attenuation which is shown to be related to absolute viscosity.

Excitation and measurement power dissipation in the coil is minimized enabling measurement of the resistance of the coil as a determinant of the temperature of the fluid.

DETAILED DESCRIPTION OF THE INVENTION

Figure 1:
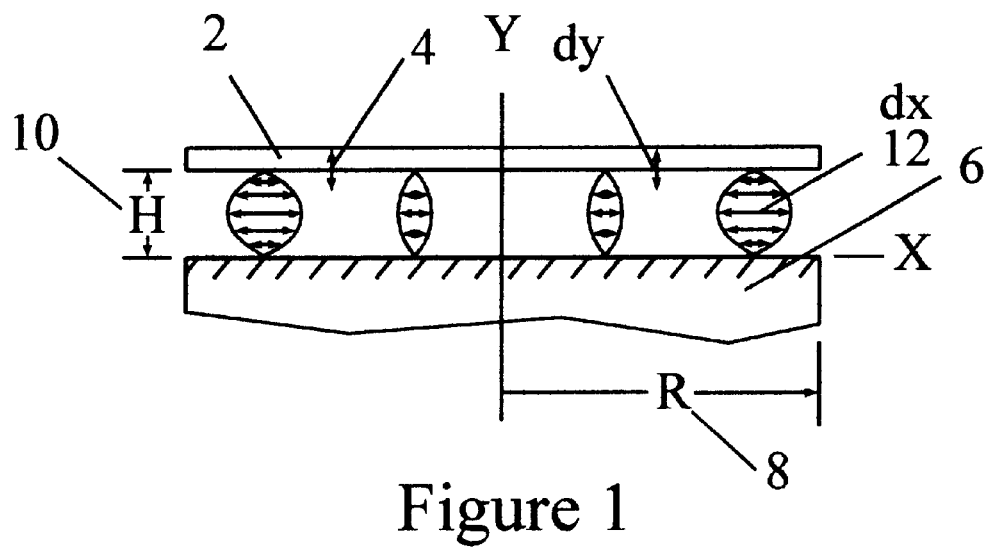
FIG. 1 is a diagram of the measurement gap between the vibrating cantilever beam and the rigid post.

In FIG. 1 a cantilever beam 2 with a rounded edge of radius R 8 is set into vibration at its natural resonant frequency by imparting a brief impulsive force. The beam vibrates with a peak-to-peak amplitude dy 4. A rigid circular post 6 of radius R 8 is positioned close to the beam, separated by a gap of magnitude H 10.

If we assume the fluid within the gap is incompressible, and that the fluid remains attached to the beam and post surfaces, motion of the fluid within the gap will assume a parabolic shape within the gap between the beam and post. The peak-to-peak amplitude of the fluid motion at the center of the gap, dx 12 will be given by $$dx = (3X/4H)dy \tag{1}$$

Recognizing that the fluid at the beam and post surface is not displaced, the shear rate S, which is the ratio of the shearing speed divided by the lateral spacing, is approximately given by $$S \sim dx/dt/(H/2) = (6x/4H^2)dy/dt \tag{2}$$

where x is the radial distance from the center. If we average this over the span of the beam and post, we find that the average shear rate <S> within the gap 10 is given by $$<S> \sim (3R/4H^2)dy/dt \tag{3}$$

Shear rate is a well known measure of the intensity with which a fluid is being stressed and a determinant in the measurement of viscosity. The implications of Equation 3 are that the shear rate in the gap between a beam vibrating in a direction normal to an approximate rigid disc is proportional to the time rate of the vibration (normal velocity) times the ratio of the radius of the disc divided by the gap height squared. Without the rigid post there would be no shear of the fluid other than that associated with flow around the edge of the vibrating beam. If we make the ratio $R/H^2$ large the shear in the fluid is increased and the shear-induced viscous damping on the beam is increased, improving the sensitivity to measurement of viscosity fluids. In a preferred embodiment to be described the ratio $3R/4H^2$ is about 176, which enables sensitive measurement of fluids in the important 5 to 50 centipoise range. The ratio $R/H^2$ can be adjusted based on the desired viscosity measurement range.

Figure 2:
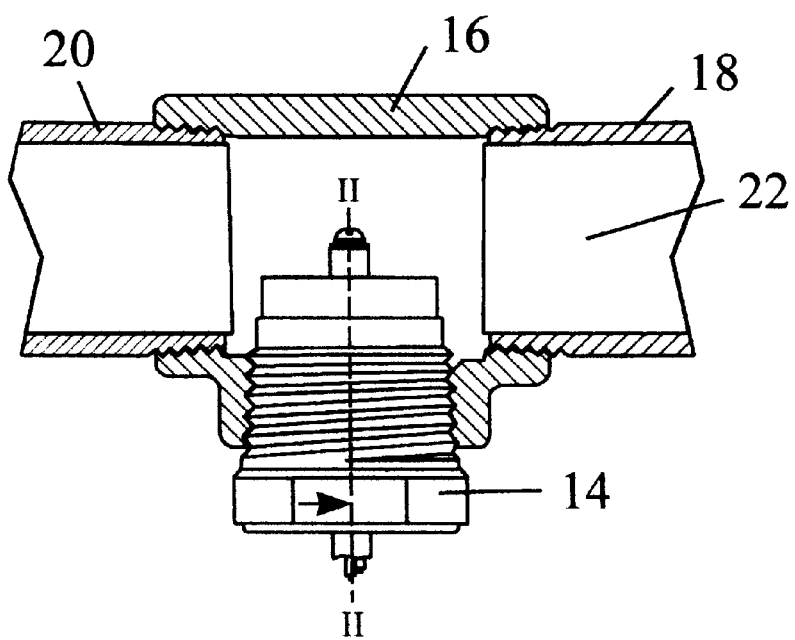
FIG. 2 shows a typical installation for process measurement in which the sensor is inserted into a line containing fluid.

In FIG. 2 there is shown a typical process viscometer installation in which a sensor 14, to be described in greater detail, is inserted into a piping network 16, 18, 20 shown in cross section. The piping carries fluid 22 to be measured. The fluid might be printing ink, fuel, lubricating oil, coating material, etc. The sensor could have also been installed into the wall of a tank or reservoir at any desired orientation using small or large lines.

Figure 3:
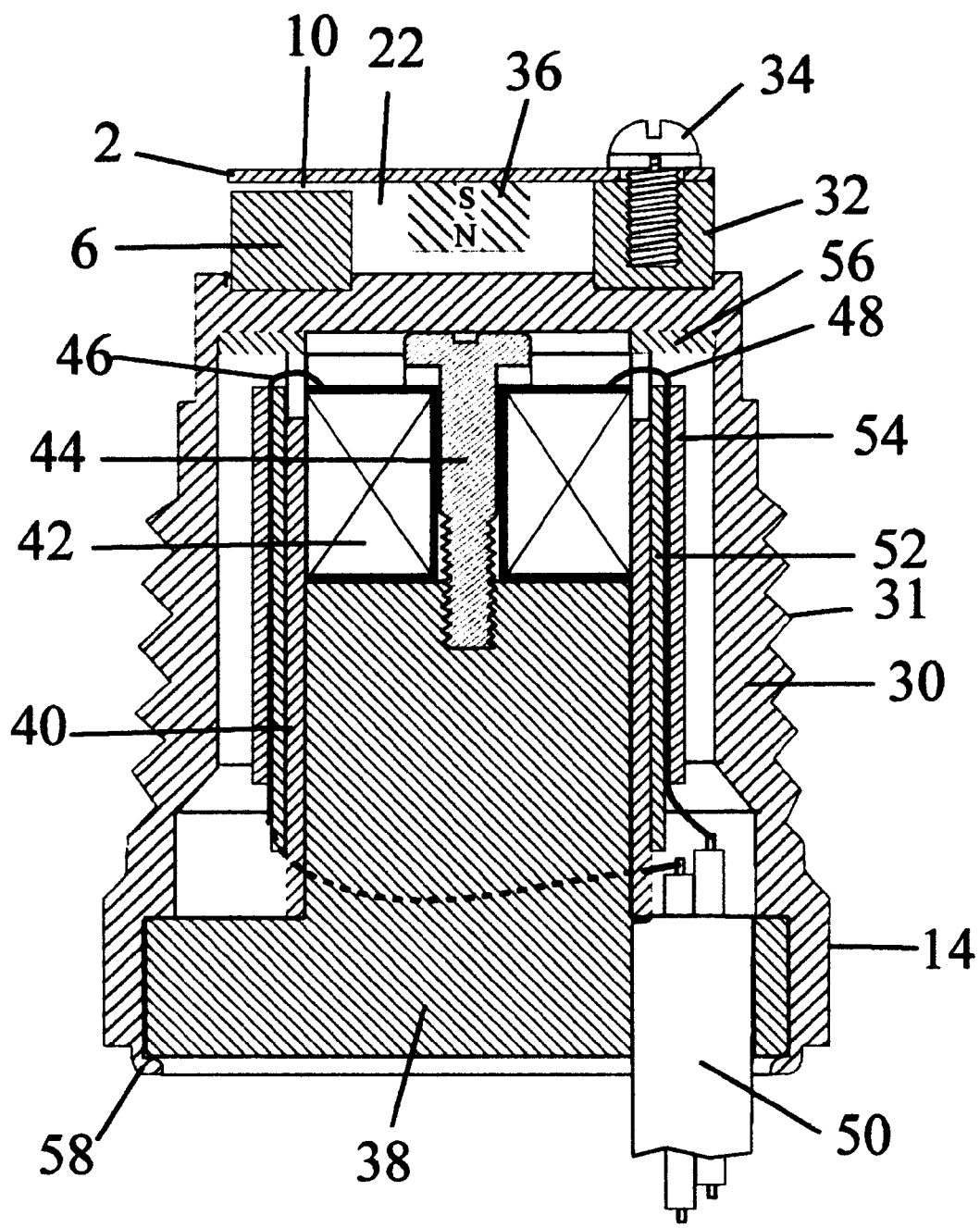
FIG. 3 shows a preferred embodiment of the sensing element in cross section.

FIG. 3 shows a sectional view of a preferred embodiment of a process viscosity sensor which illustrates the principle of measurement by normal vibration in proximity to a rigid post. The figure is a sectional view along the line II—II of FIG. 2. The sensor is housed in a body element 30, with threaded means 31 for insertion into the piping component 16. The body 30 is fabricated from corrosion resistant, low-magnetic permeability material such as type 316L stainless steel. The mounting threads 31 are, for example, ¾-inch NPT threads. On the front face of the body there is a 0.188-inch diameter post 32 for support of a flexible cantilever beam 2. The post 32 and the beam 2 are fabricated from corrosion resistant but magnetically permeable material such as type 430 stainless steel. The cantilever beam 2 is retained on the support post 32 with a stainless steel retaining screw and lock washer 34. A permanent magnet 36 is mounted on the center of the beam facing the sensor body. A rigid post 6 is mounted on the body of the sensor at the far end of the beam 2. The rigid post 6 is sized so as to produce a small gap 10, say 0.020 inch. The rigid post 6 is made of a magnetically permeable, but corrosion resistant material such as 430 stainless steel and is 0.188 inch in diameter. The support post 32 and rigid measurement post 6 can be joined to the body element 30 by brazing or welding.

Inside the sensor there is a T-shaped back 38, which is fabricated from magnetically permeable material such as carbon steel or 430 stainless steel. A magnetically permeable tubular sleeve 40 is pressed onto the back. The sleeve 40 forms a cavity which supports a coil 42, consisting of perhaps 1400 turns of AWG38 magnet wire. The coil is retained with a magnetically permeable retaining screw with lock washer 44. There are two leads from the coil 46 and 48 which are connected to the two conductors of a cable 50 passing through access slots 47 and 49 in the sleeve. The cable can be a twisted pair or a coaxial type. An electrically insulating layer 52 such as polyimide tape is applied to the sleeve to insulate the lead wire 48 from the sleeve 40 and an overlay of insulating tape 54 is also used to mechanically support the two lead wires 46 and 48. A disc 56 made of magnetically permeable material such as carbon steel or 430 stainless steel completes the magnetic circuit. The edge of the body 30 adjacent to the back 38 is crimped or rolled 58 to retain the back inside the body.

Figure 4:
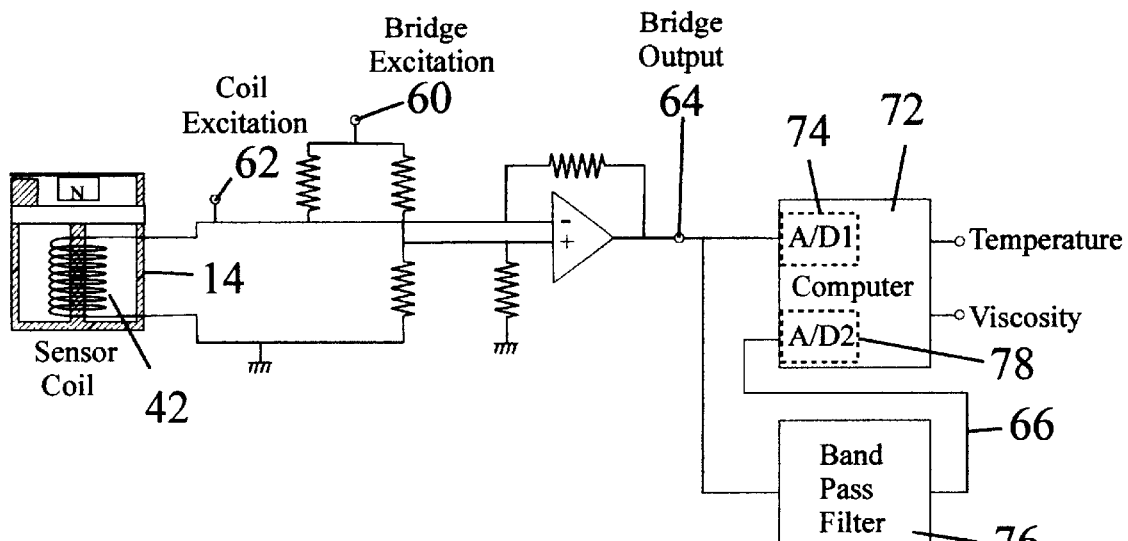
FIG. 4 shows the sensor excitation points, filtering and computational relationships.
Figure 5:
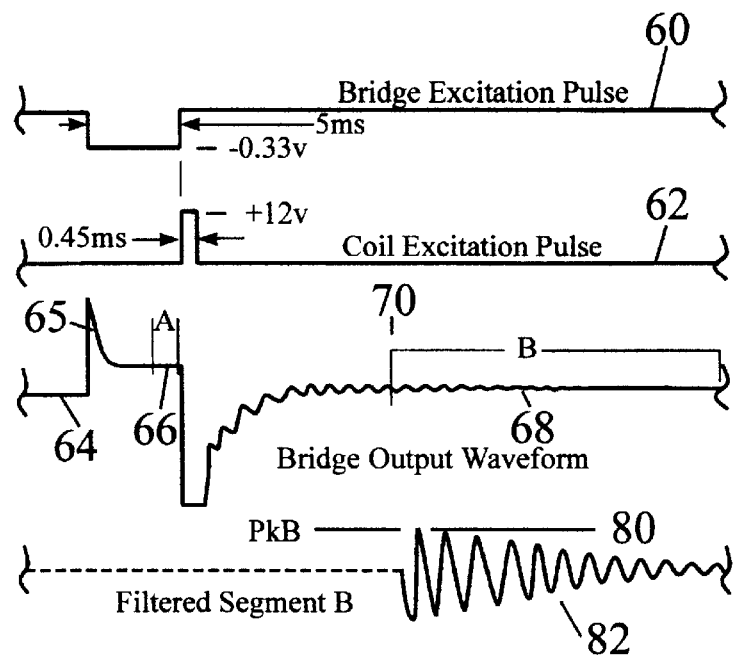
FIG. 5 shows typical excitation and measurement waveforms.

FIG. 4 illustrates a preferred embodiment of the excitation and measurement circuitry for the sensor 14. The coil 42 within the sensor constitutes one leg of a Wheatstone bridge. To initiate a measurement a low level pulse 60 of perhaps 5 milliseconds duration is imposed on the bridge. Immediately after cessation of the bridge excitation pulse a coil excitation pulse 62 is imposed directly on the coil. In a preferred embodiment this pulse is perhaps 0.45 milliseconds in duration and twelve volts. As a result of the excitation pulses the output waveform has the response 64 which has two segments of measurement interest.

Figure 6:
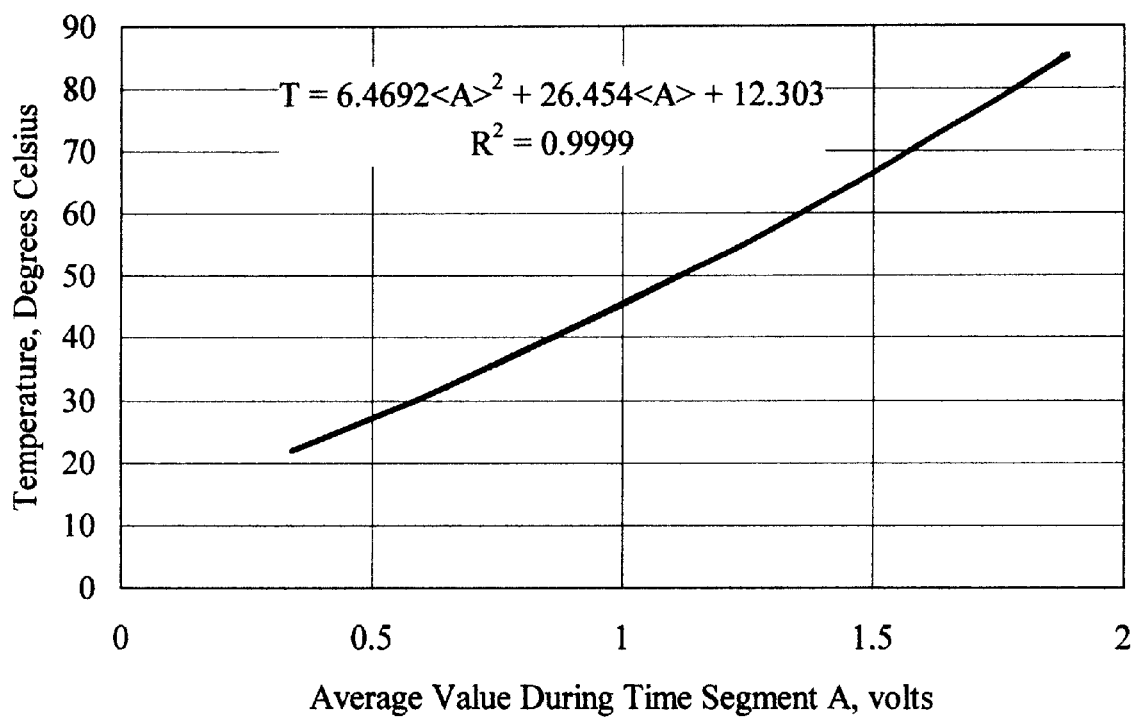
FIG. 6 illustrates a typical relationship between the average value of the output waveform during time segment 66 and the temperature in degrees Celsius.

The first segment 66, labeled A, is chosen to be well after the initial inductive transient 65 yet prior to the end of the initial bridge excitation pulse. For example, time segment 66 might be chosen to persist from 4.4 to 4.8 milliseconds. Waveform 64 is sampled on two channels of a computer 72. In FIG. 4 the unfiltered waveform 64 is sampled by input Analog/Digital converter A/D1 74. If the sampling interval is at a rate of 50 kiloHertz, the samples during time segment 66 would be samples 220 through 240. To determine temperature of the sensor immersed in the flowing fluid, the average of the samples during time segment 66 is compared to a calibration curve of the sort illustrated in FIG. 6. This is a reliable indicator of temperature because bridge and coil excitation pulses and their repetition frequency are chosen to produce negligible heat, and the circuit components are sized to result in an output during time segment 66, which is within the measurement span of the electronics for the temperatures of interest. This is easily accomplished by one skilled in the art. After computation of the temperature, the computer outputs this information in the usual fashion such as through a serial port, or as an analog signal such as 0 to 5 Volts, or 4 to 20 milliamps.

The coil excitation pulse, 62, creates a brief magnetic force on the cantilever beam 2. The beam stiffness and mass are chosen so that the beam and magnet will resonate at a low frequency so that the fluid will have time to thoroughly stabilize throughout the gap 10 during each cycle, i.e. the acoustic wavelengths in the fluid at the resonant frequency are very large compared to the dimensions of the gap. For example, in the preferred embodiment the beam oscillates at about 900 Hertz. Duration of the coil excitation pulse 62 is chosen to be approximately one-half the period of the natural oscillation of the beam, for example, 0.45 milliseconds in the preferred embodiment. Magnetic coupling of the coil to the beam is enhanced by the magnetic circuit consisting of retaining screw 44, back element 38, sleeve 40, spacer 56, mounting post 32, measurement post 6, beam element 2, and magnet 36. These items in the magnetic circuit should be fabricated from materials with a magnetic permeability many times that of free space. Examples include carbon steel, iron, and 430 stainless steel.

After impulsive excitation of the beam, it is free to oscillate at its resonant frequency. As noted previously, the oscillations of the beam 2 will be attenuated by viscous shear in the gap 10. In the preferred embodiment I include a band pass filter with gain 76. The band pass filter is set to readily pass frequencies in the vicinity of the resonant frequency of the beam but reject all other frequencies. The filter is shown as a discrete hardware element for ease of understanding, but it could be realized in software within the computer. The output of the filter 76 is sampled by the Analog to Digital converter AD2 78. Output of the filtered waveform prior to the beginning of time segment B 70 is of little interest, since it is corrupted by the effects of the excitation pulse on the circuitry. The attenuation of the filtered and amplified waveform 82, is a good measure of the viscosity of the fluid within the measurement gap 10. There are many ways in which the attenuation might be determined. In the preferred embodiment I have found that one of the most accurate and simplest is to record the amplitude of the first peak of waveform B, 80. The first peak is an indicator of the attenuation because the time onset of time segment B has been significantly delayed vis-à-vis the excitation time, for example, by 13 milliseconds, during which time the beam has undergone about 12 oscillations. If this technique is used, care should be exercised to maintain the amplitude and duration of the exciting impulse 62. Alternative techniques include taking the ratio of successive peaks, as would be apparent to one skilled in the art.

Figure 7:
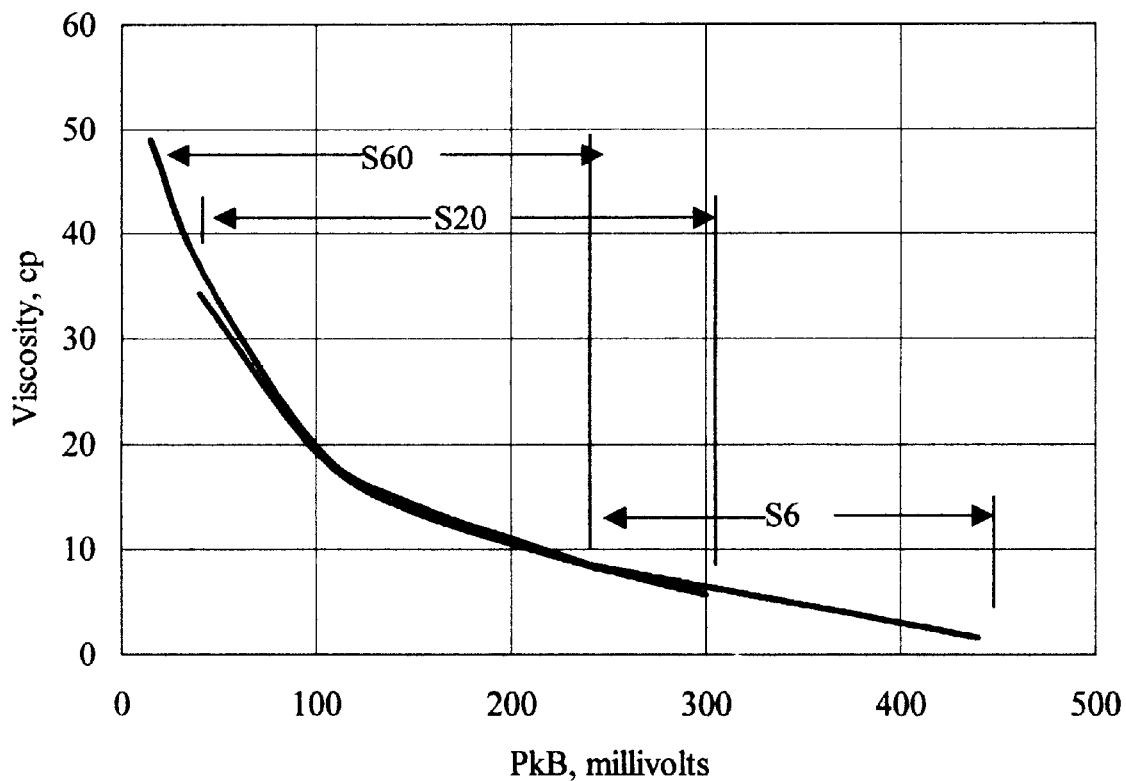
FIG. 7 shows a typical relationship between the peak value of the filtered output during time segment 68 and fluid viscosity over the range 5–50 centipoise.

FIG. 7 shows a graphical summary of tests in which a viscometer of the preferred design was exposed to three different reference fluids. The calibration reference fluids chosen were S60, S20, and S6 from Cannon Instrument Company, State College, Pa. Each of these fluids has a well known viscosity versus temperature relationship carefully measured by the supplier using precision laboratory techniques. With each fluid the sensor and fluid were heated to temperatures between 20 degrees Celsius and 85 degrees Celsius. Each calibration fluid has a different absolute viscosity at a given temperature. For example, at 55 degrees Celsius S60, S20, and S6 have viscosities of 24, 8.9, and 2.8 centipoise respectively.

Using a single polynomial relationship which was essentially the mean of the curves shown in FIG. 7, I found that the measured viscosity for the three reference fluids overlay one another. The implication is that in spite of substantially different temperatures and fluid densities, the peak of segment B 80 is an accurate measure of absolute viscosity within the range 5 to 50 centipoise. For instance, to achieve about 9 centipoise, it was necessary to heat S60 to 84.8 degrees Celsius, S20 to 54.7 degrees Celsius, and S6 to 21.4 degrees Celsius. Nevertheless, in all three cases the recorded peak value 80 was substantially identical. This was the only triple point, but from 6 to over 30 centipoise there was good double correspondence as evidenced by the fact that the two curves are virtually indistinguishable.

Figure 8:
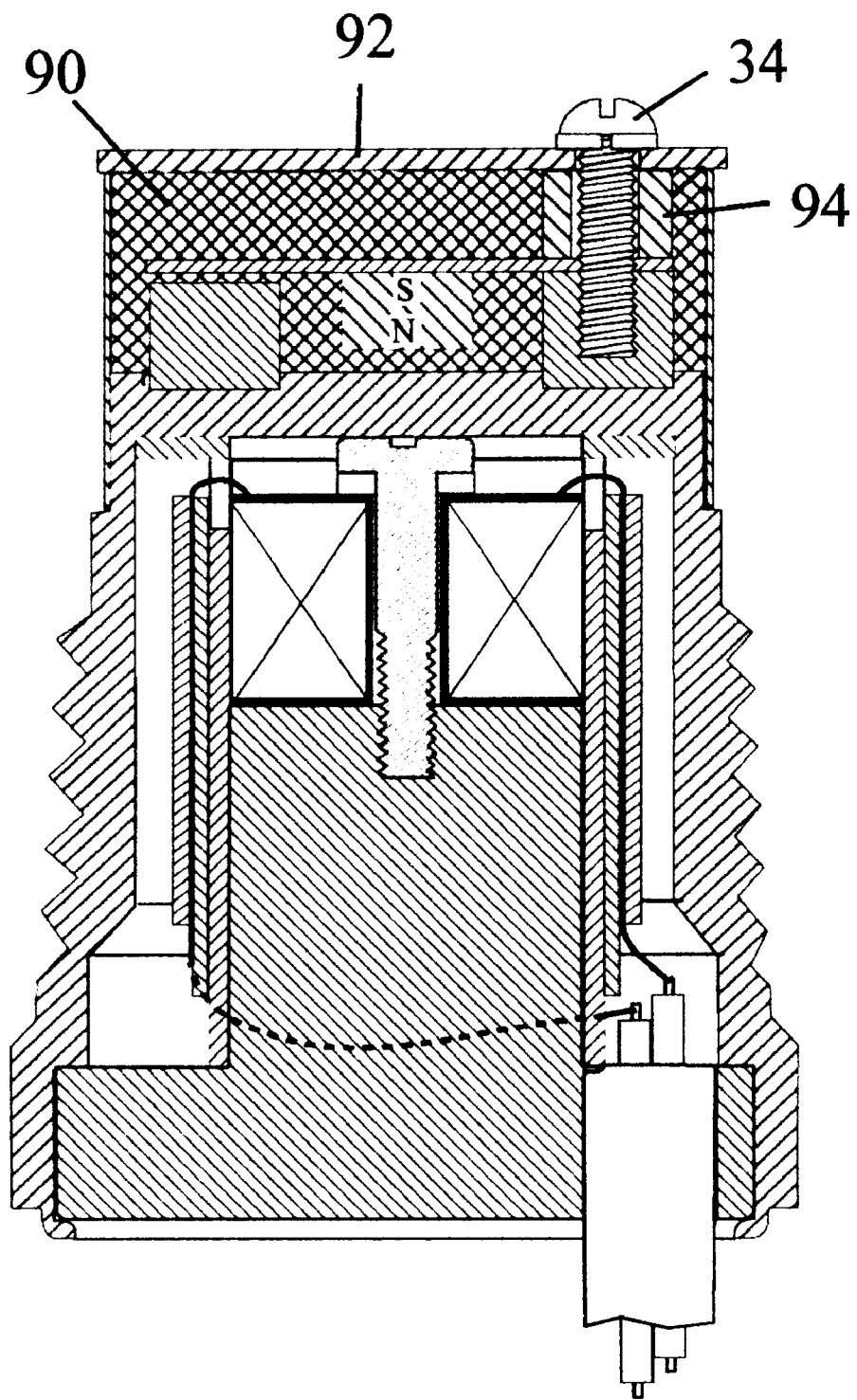
FIG. 8 shows an embodiment of the device which incorporates a protective screen 90 for the purpose of magnetic shielding and elimination of large particles from the measurement region.

FIG. 8 shows the addition of a protective screen 90 for improved electromagnetic shielding and protection of the measurement beam and gap from particulates within the process stream. The screen is retained by a cap 92 which is supported by a spacer 94. In this case the mounting screw 34 would be extended. The mesh of the screen would be chosen to pass fluid yet block particulates that might interfere within the measurement gap. Additional support posts might also be used.

Design alternatives to the preferred embodiment are of course possible, and fall within the intended scope of the device. For example, the measurement post could be the same as the support post resulting in a nil gap. In this case the beam might be creased so as to be a flexible end-supported beam rather than a cantilever beam. In this case the measurement gap would be the space between the magnet and the face of the device, so the height of the support posts would be adjusted accordingly. Other variations will be apparent to those skilled in the art.

What is claimed is:

1. A viscosity sensing device consisting of:
 a flexible beam immersed in a fluid,
 impulsive means to initiate resonant oscillation of the beam,
 a rigid surface oriented perpendicular to the direction of oscillation of the beam in close proximity to at least a portion of the beam positioned and spaced so as to substantially affect the viscous attenuation of the beam vibration,
 circuitry to determine the resultant rate of decay of the beam oscillations,
 computational means to relate the rate of oscillation decay to viscosity,
 and output devices to enable access to the computed result.

2. A viscometer as defined in claim 1 wherein:
 the flexible beam is of cantilever design.

3. A viscometer as defined in claim 1 wherein:
 the means of initiating a resonant oscillation of the beam involves the use of a magnetically permeable beam in proximity to an electrical coil, wherein a brief but intense current is circulated through the coil.

4. A viscometer as defined in claim 3 in which
 a permanent magnet is affixed to the flexible beam to improve magnetic coupling between the coil and the beam and to create electromotive force in the coil as the beam oscillates.

5. A viscometer as defined in claim 4 in which
 the magnetic coupling between the coil and the oscillating beam is further enhanced by the use of a magnetic circuit consisting of magnetically permeable materials that link the inside of the coil to one side of the magnet with a return path to the extremities of the beam and thence to the other side of the magnet.

6. A viscometer as defined in claim 3 in which
 the heat dissipated in the coil by activation circuitry is sufficiently modest as to result in a negligible temperature rise in the coil, thereby enabling, by measuring the resistance of the coil, a determination of the coil temperature and by implication the temperature of the adjacent fluid.

7. A viscometer as defined in claim 6 in which
 the resistance of the coil is determined by using the coil as one leg of a bridge circuit, powering the bridge with a low level voltage, then after decay of transients measuring the output level of the bridge and relating this level to temperature using computational means.

8. A viscometer as defined in claim 1 in which
 the face of the device including the flexible beam is encased in a porous screen suitable for electromagnetic shielding with holes sized to readily pass the fluid yet screen out particles comparable to or greater than the gap between the flexible screen and the rigid surface.

9. A viscometer consisting of:
 a magnetically permeable and flexible beam supported near the face of the device,
 a permanent magnet mounted on the beam facing the device,
 means to immerse the face of the device in a fluid,
 a coil within the device magnetically coupled to the flexible beam and magnet,
 excitation circuitry which periodically forces a brief burst of current in the coil creating an impulsive magnetic force on the beam and magnet, inducing natural oscillations, the duration of the excitation being approximately one-half the period of the natural oscillation,
 a rigid surface oriented perpendicular to the direction of oscillation of the beam in close proximity to at least a portion of the beam positioned and spaced so as to substantially affect the viscous attenuation of the beam vibration,
 circuitry to detect the electromotive force induced in the coil as a result of oscillation of the beam and magnet, including amplification and frequency selective filtering, computational means for measuring the rate of decay of the beam oscillations and relating the rate of decay to viscosity and circuitry to output the computed viscosity in a useful format.

10. A viscometer as defined in claim 9 wherein:

the flexible beam is of a cantilever design.

11. A viscometer as defined in claim 9 in which the magnetic coupling between the coil and the oscillating beam with magnet is further enhanced by the use of a magnetic circuit consisting of highly permeable materials that link the inside of the coil to one side of the magnet with a magnetically permeable return path to the extremities of the beam and thence to the other side of the magnet.

12. A viscometer as defined in claim 9 in which the face of the device including the flexible beam is encased in a porous screen suitable for electromagnetic shielding with holes sized to readily pass the fluid yet screen out particles comparable to or greater than the gap between the flexible screen and the rigid surface.

13. A viscometer as defined in claim 9 in which the heat dissipated in the coil by activation circuitry is sufficiently modest as to result in a negligible temperature rise in the coil, thereby enabling, by measuring the resistance of the coil, a determination of the coil temperature and by implication the temperature of the adjacent fluid.

14. A viscometer as defined in claim 11 in which the resistance of the coil is determined by using the coil as one leg of a bridge circuit, powering the bridge with a low level voltage, then after decay of transients measuring the output level of the bridge and relating this level to temperature using computational means.

* * * * *